(12) United States Patent
Levy

(10) Patent No.: US 12,150,680 B2
(45) Date of Patent: *Nov. 26, 2024

(54) SURGICAL NAIL HAVING A FIXATION BRACKET

(71) Applicant: Michael S. Levy, Cherry Hill, NJ (US)

(72) Inventor: Michael S. Levy, Cherry Hill, NJ (US)

( * ) Notice: Subject to any disclaimer, the term of this patent is extended or adjusted under 35 U.S.C. 154(b) by 226 days.

This patent is subject to a terminal disclaimer.

(21) Appl. No.: 17/009,431

(22) Filed: Sep. 1, 2020

(65) Prior Publication Data

US 2021/0085376 A1    Mar. 25, 2021

Related U.S. Application Data

(63) Continuation of application No. 15/913,007, filed on Mar. 6, 2018, now Pat. No. 10,758,279, which is a continuation of application No. 15/222,430, filed on Jul. 28, 2016, now Pat. No. 9,907,586.

(51) Int. Cl.
*A61B 17/72* (2006.01)
*A61B 17/06* (2006.01)

(52) U.S. Cl.
CPC ........ *A61B 17/72* (2013.01); *A61B 17/06166* (2013.01)

(58) Field of Classification Search
CPC ............ A61B 17/7233; A61B 17/7241; A61B 17/7283; A61B 17/7208; A61B 17/744; A61B 17/746; A61B 17/72
See application file for complete search history.

(56) References Cited

U.S. PATENT DOCUMENTS

| 5,443,466 A * | 8/1995 | Shah ...................... A61B 17/72 606/62 |
| 2006/0189987 A1* | 8/2006 | Orbay ................ A61B 17/8047 606/62 |

FOREIGN PATENT DOCUMENTS

| FR | 2781360 A1 * | 1/2000 | ......... A61B 17/7233 |
| FR | 2948555 A1 * | 2/2011 | ......... A61B 17/7233 |

* cited by examiner

*Primary Examiner* — Julianna N Harvey
(74) *Attorney, Agent, or Firm* — Lauletta Birnbaum LLC

(57) ABSTRACT

A nail device for fixing proximal bone fractures and muscle tears. The nail device includes a flexible nail adapted to be inserted into a bone and a fixation bracket attached to the nail adapted to repair soft tissue injuries.

13 Claims, 13 Drawing Sheets

SURGICAL NAIL HAVING A FIXATION BRACKET

CROSS-REFERENCE TO RELATED APPLICATIONS

This application claims priority to U.S. patent application Ser. No. 15/222,430, filed Jul. 28, 2016 and now U.S. Pat. No. 9,907,586 and U.S. patent application Ser. No. 15/913,007, filed Mar. 6, 2018; and now U.S. Pat. No. 10,758,279.

STATEMENT REGARDING FEDERALLY SPONSORED RESEARCH OR DEVELOPMENT

The present invention was not developed with the use of any Federal Funds, but was developed independently by the inventors.

BACKGROUND

1. Field

The present invention relates generally to the field of bone nail technologies, and more specifically to a nail for fixing proximal fractures and having a bracket for fixing muscle tears for the humerus, clavicle, radius, and fibula bones.

2. Background

Proximal humeral fractures and rotator cuff tears typically occur together at increasing rates. Age, the mechanism of injury, and dislocations at the time of injury are all risk factors for soft tissue disruption around the bone, such as rotator cuff tears, that may be present with fractures of the humerus in the same region.

There exist devices and techniques that can fix humeral fracture, both proximal ones and fractures in the shaft. There are even ways to fix the soft tissue and hold it in place while bone healing takes place. However, there is currently no intramedullary implant or implant system that can accomplish all of the injury patterns utilizing the same set of implants. Current systems require basically two different surgeries, one to fix the bone and another to fix the soft tissue. This adds time to the case, and it adds additional set ups (sterile cases and increased set up time for the operation). The use of one system/implant can help streamline both the operative time and the operative set up.

As a general surgical rule, any advance either by technique or by implants that can simplify complex suturing techniques and still perform clinically can be a significant advantage. The technique and implants of the present invention can accomplish this by holding the sutures that repair soft tissue to the implant. Fewer holes are needed in the bone to pass the suture through. This reduces the trauma to the already fractured bone. In addition, the use of flexible nails permits smaller incisions. Using an attached bracket also helps reduce the incision, by allowing sutures to be tied and fixed to one central point.

With respect to the clavicle, there is no existing implant that combines fixation of bone with soft tissue and ligament fixation. A surgeon can place a plate on the bone or nail the bone to fix the fracture. The clavicle has ligaments that are torn that lie under the fractured bone. Typically, the soft tissues and ligaments are torn off the ends of the bone and in order to repair disrupted ligaments sutures and repair techniques either have to be done through small holes made in the bone or direct repair to other soft tissues around the clavicle must be done. If sutures are passed from one side of the bone to another an anatomic repair is almost always impossible to achieve due to tension and position of the torn structures.

With respect to the radius, radius nails exist that have extensions for soft tissue; however, none have a separate tab.

For the Tibia and Fibula, there exist ways to repair lateral ligaments of the ankle, such as suture repairs and bone anchors. There are also ways to repair the syndesmosis. Mostly syndesmosis repairs take place with screws either directly bones to bone, or with a lateral fibula plate, which may be holding a fracture together. A fiber wire tight rope exists which does not need to be removed. In contrast, syndesmosis screws need to be removed or they will break over time.

Thus, a need exists for an implant device having an intramedullary fixation a tab to aid in repair of the soft tissue. To accomplish intramedullary fixation with an external soft tissue tab, the following are required: Intramedullary fixation, an inter splint. (depending on the biomechanics of the bone and problem requiring a solution a screw or a series of screws can also be implanted to get solid reliable bone fixation), a connector, a tab, healing the bone to metal, and healing soft tissue to metal.

In the case of the humerus, a need exists for a humeral nail device, that in the same system of implants can provide for humeral fracture proximal fixation, humeral fracture shaft fixation, and soft tissue repair of rotator cuff tears. The nail of the present invention is intended to be employed for fixation of both proximal humeral fractures (around the shoulder), and fractures of the humeral shaft (the tube part of the arm bone). Additionally, the nail can aid in repair of the soft tissue around a proximal humeral fracture (such as a rotator cuff tear). This nail can also be employed when trauma to the shoulder includes both proximal humerus fractures (around the shoulder) and rotator cuff tears. This present invention solves three humeral injury patterns (proximal humeral fractures, humeral shaft fractures, and proximal humeral fractures that also require rotator cuff repairs). The invention includes the combination of at least three unique designs: a flexible nail for fixing proximal humeral fractures, a humeral shaft fracture nail that controls fixation distally without cross locking and an intramedullary nail devices that can also fix rotator cuff tears.

For the clavicle, clavicle device to hold the fracture while healing such as an internal splint. On the lateral end a tab will be held in place by the clavicle implant and reach toward the undersurface and medial to secure the coracoclavicular ligaments. For the radius, a radius tab is connected to a nail and be exposed on the volar surface to accept sutures to repair and hole volar ligaments the help support the radio-carpal joint.

For the fibula, the fibula tab is held in place by a nail and wraps forward to help secure the anterior talofibular ligament.

SUMMARY

A nail device for fixing fractures and muscle tears. The nail device includes a flexible nail adapted to be inserted into a bone and a fixation bracket attached to the nail adapted to repair soft tissue injuries. The flexible nail may comprise an elongated unitary or integral cannulated body having a head portion, a distal tip portion, and an angled frustoconical intermediate body portion that connects the head portion to the distal tip portion. The fixation bracket may comprise a top planar leg and an inclined lateral leg connected thereto, a plurality of suture holes are provided in the lateral leg. A plurality of screw receiving openings may be located along the length of the nail head. And, the nail may be made from a titanium alloy, or stainless steel, or carbon fiber, material.

A connector may be provided between a lower surface of the top leg and an end of the nail head, wherein the nail head is secured to the fixation bracket. The connector may be dovetailed.

BRIEF DESCRIPTION OF THE DRAWINGS

The embodiments will be described in detail with reference to the following drawings in which like reference numerals refer to like elements wherein.

DETAILED DESCRIPTION

As a preliminary matter, the set of implants according to the present invention all rely on intramedullary fixation. Either an internal splint, if you will, or solid reliable screw fixation to the bone when strong reliable anchoring is required. The present system of implants relies not only on good adherence and ingrowth into bone, but also good soft tissue ingrowth and compatibility. The system overcomes this problem by utilizing titanium technology. Titanium has material properties suitable for bone implants and can manufactured using 3-D printers into any shape and surfaces can be fabricated quickly and easily.

In addition, three-dimensional printing is a new technology not just for specialties to get a specific shape, but also in total joints and trauma to develop reproducible exterior surface to help both bone and soft tissue grow into the metal and heal. Titanium and ceramic composites are utilized using this novel 3-dimensional technologies for fixation and bone and soft tissue growth. The present invention, uses a tab for fixation on both sides. Not only does the implant have to be close to bone and heal, it also has to have the ability for the repair of soft tissue to hold and heal to metal.

With or without a fracture the present set of devices links intramedullary implants with soft tissue repair tabs. Bone to metal healing and then on the other side of the tab soft tissue to metal adherence and healing.

The Humeral Nail

FIGS. 1-6 show a humeral nail device 10 for fixing proximal humerus fractures and rotator cuff tears in accordance with a preferred embodiment of the present invention. The nail device 10 includes a flexible proximal humerus nail 12 and an attached fixation bracket 14.

The humeral nail device 10 is intended for metaphyseal (proximal) humeral fractures with or without soft tissue rupture and injury. In addition, the humeral nail device 10 is also intended to be used for diaphysel (shaft) fractures as well.

Figure 1:
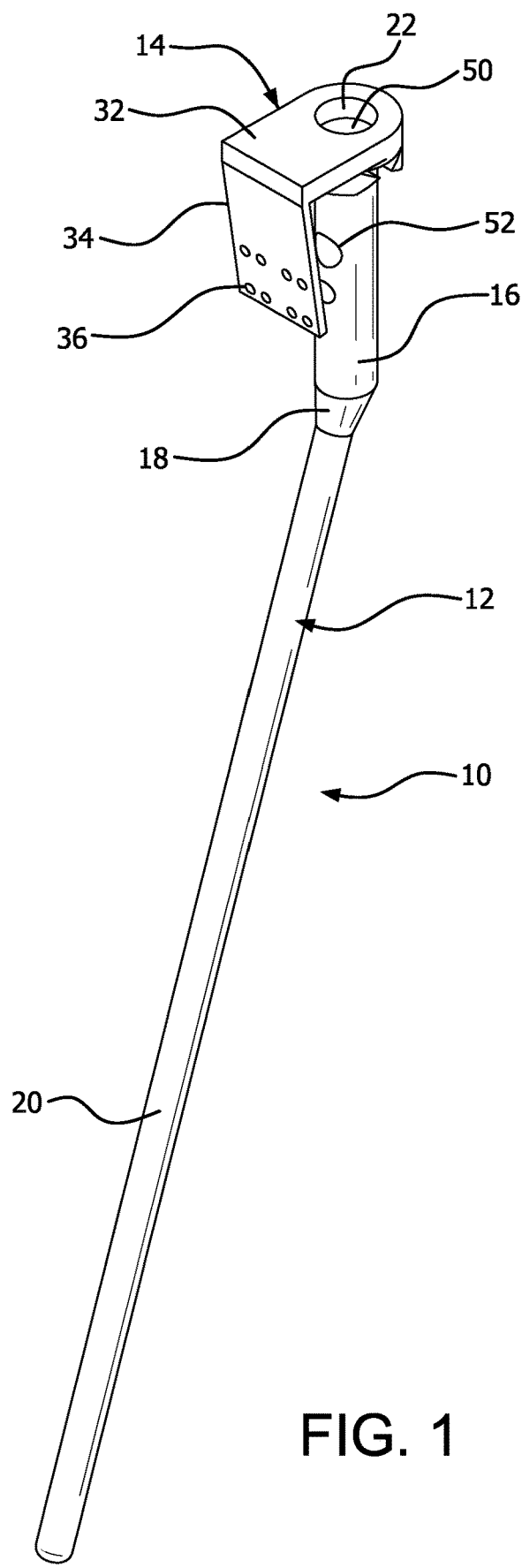
FIG. 1 is a front isometric view of a humeral nail device in accordance with the present invention.
Figure 2:
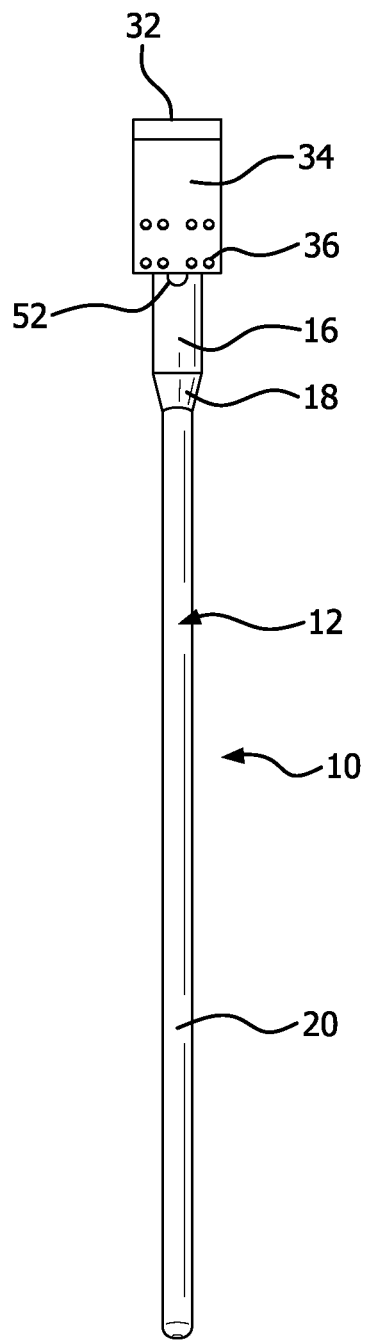
FIG. 2 is a front view of the humeral nail device of FIG. 1.
Figure 3:
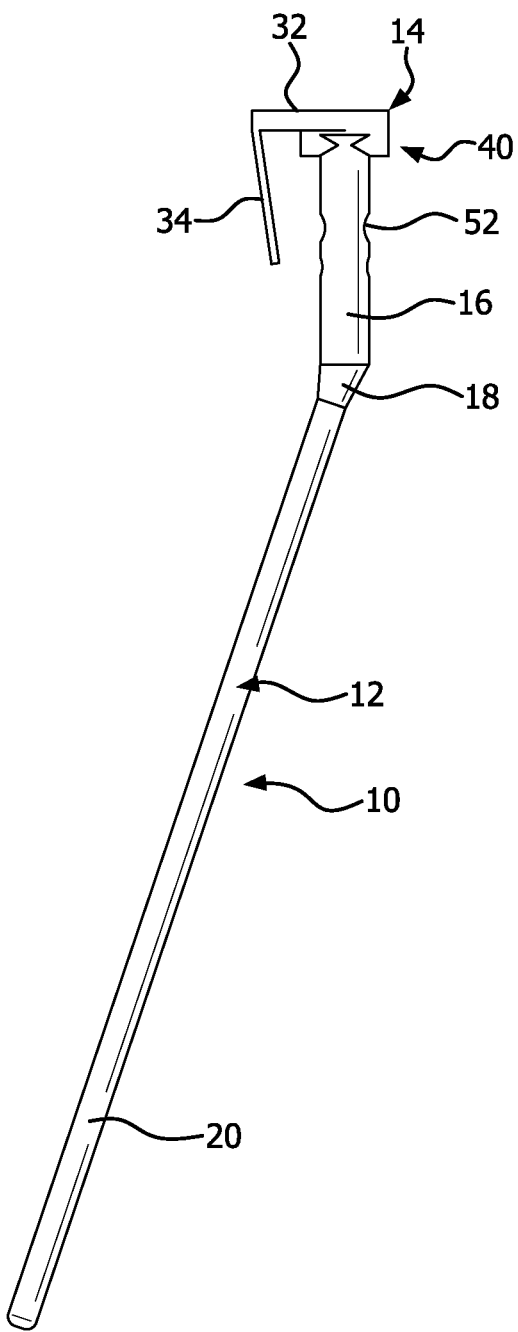
FIG. 3 is a side view of the humeral nail device of FIG. 1.
Figures 4, 5:
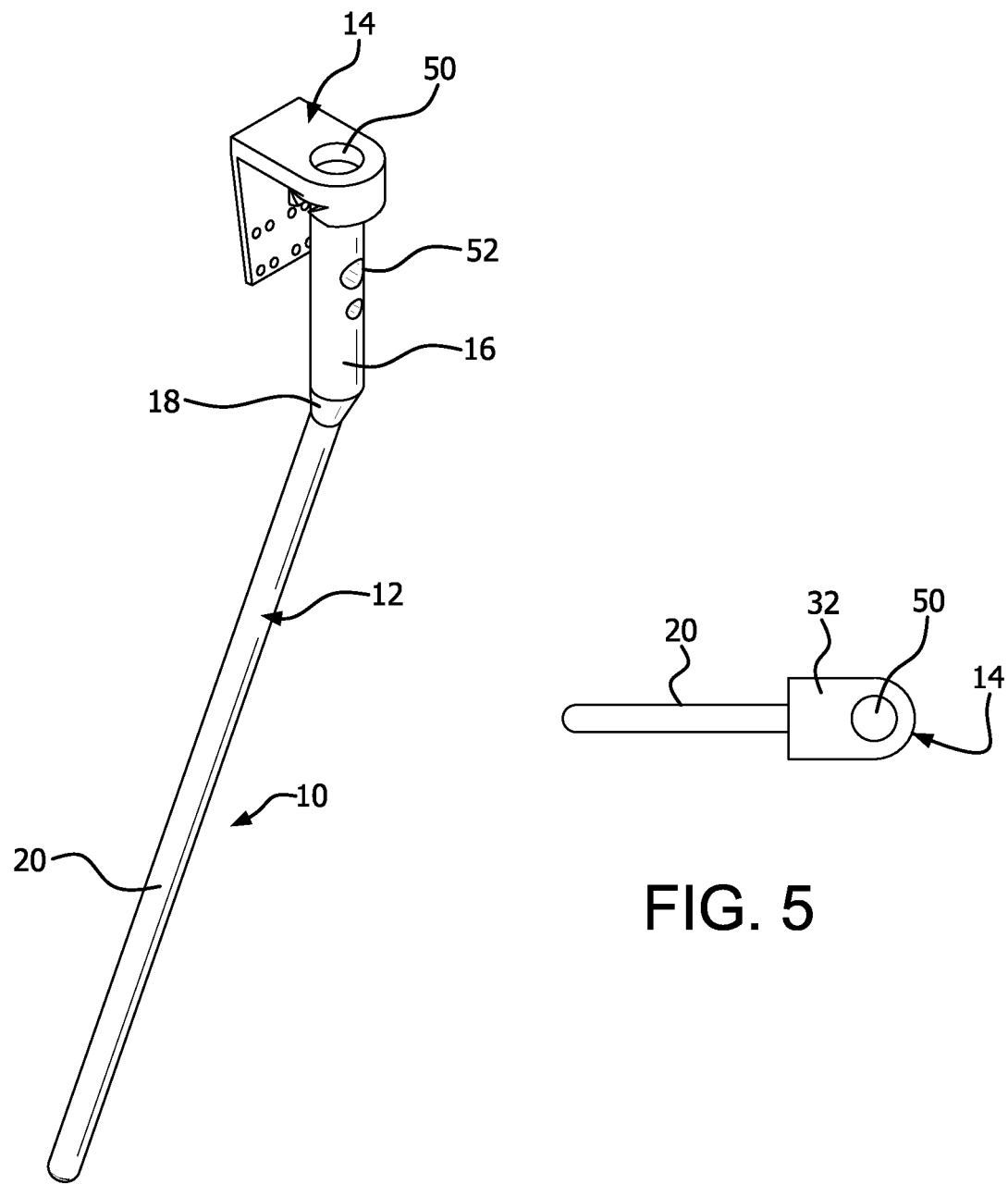
FIG. 4 is a rear isometric view of the humeral nail device of FIG. 1.
FIG. 5 is a top view of the humeral nail device of FIG. 1.
Figure 6:
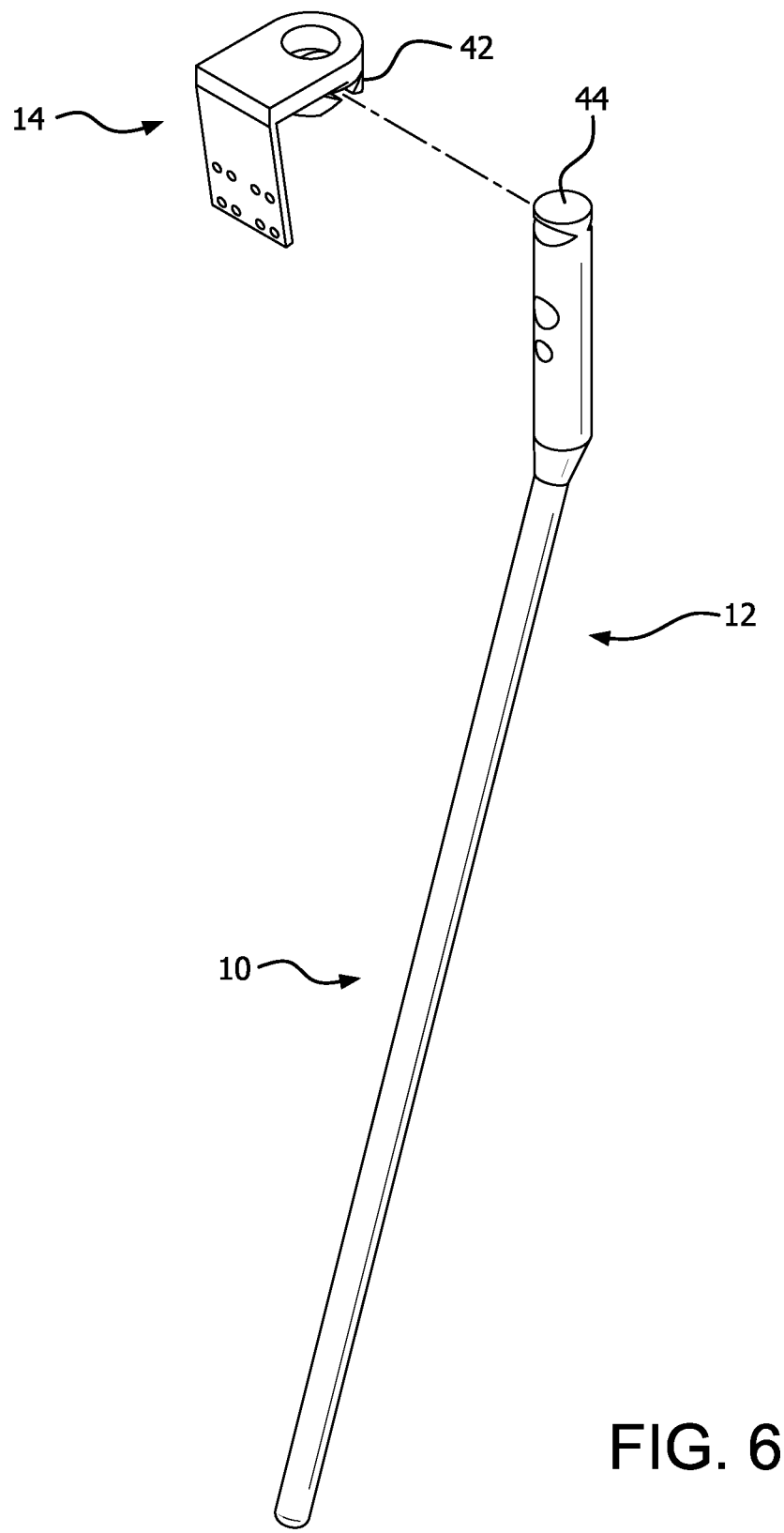
FIG. 6 is an exploded isometric view of the humeral nail device of FIG. 1.
Figure 7:
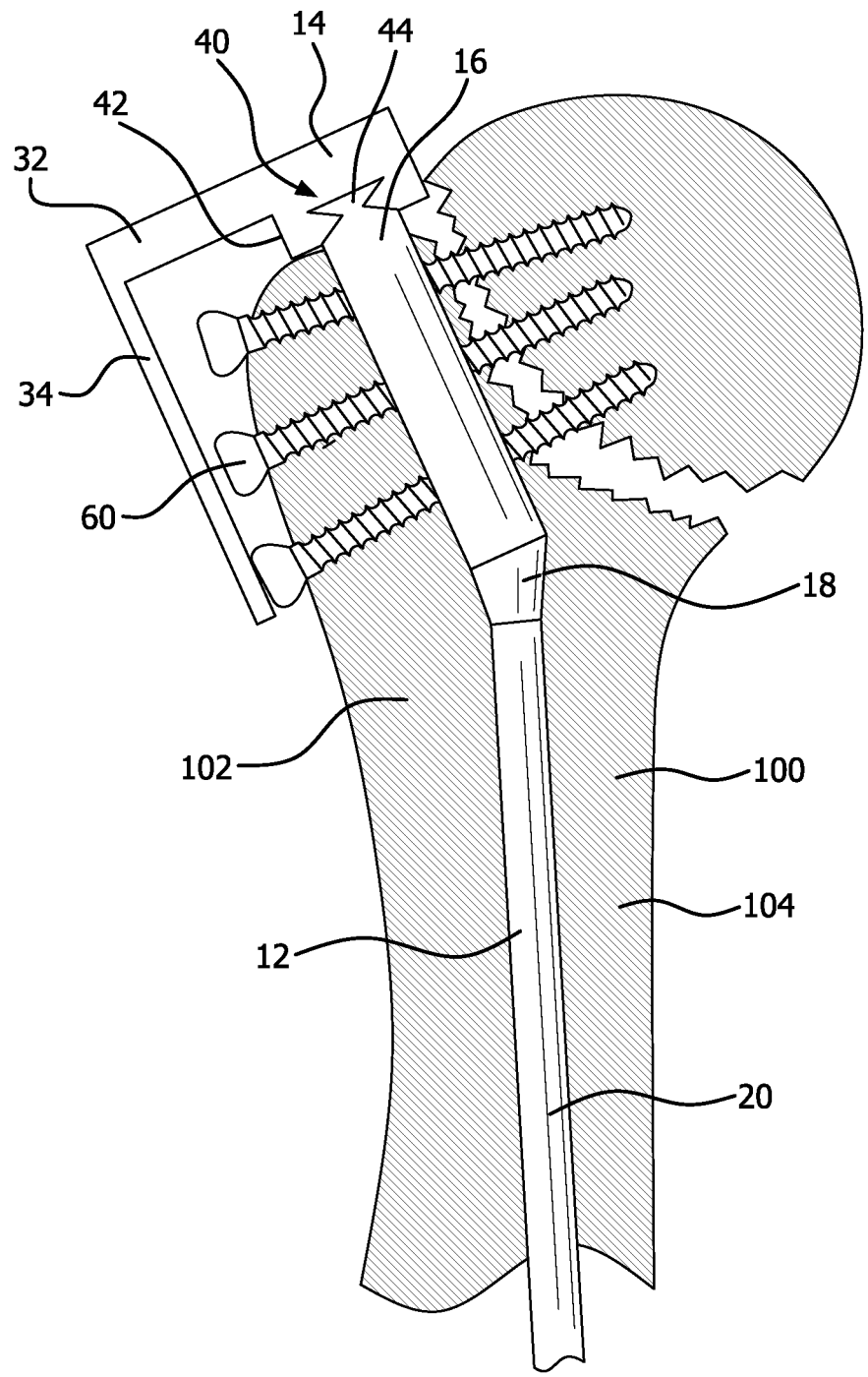
FIG. 7 is a side view of the humeral nail device of FIG. 1 in use.
Figure 8:
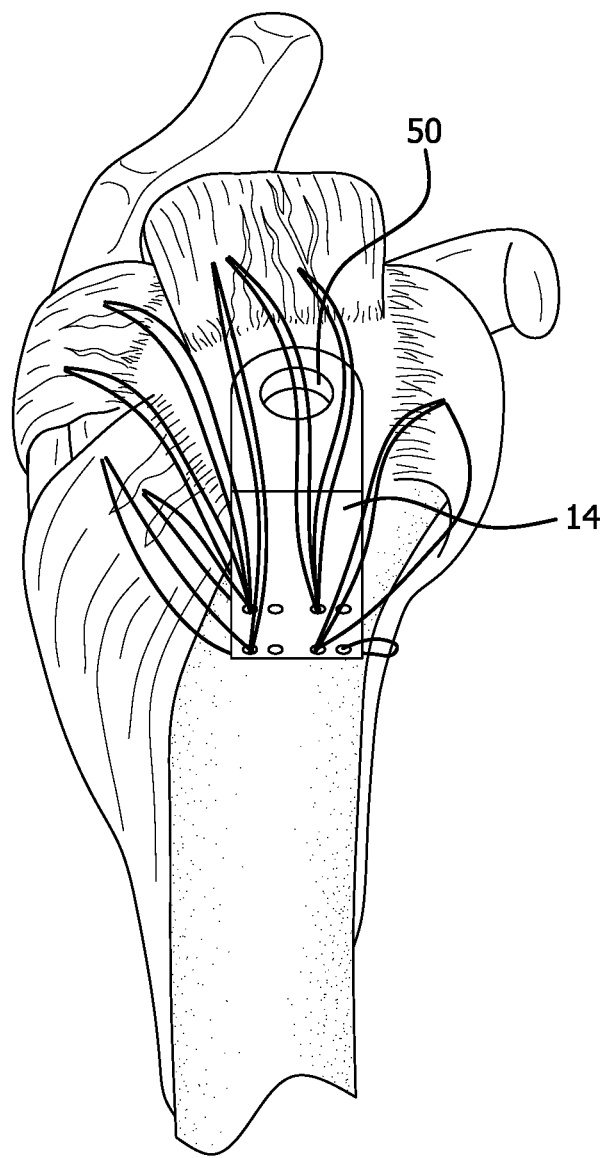
FIG. 8 is a front view of the humeral nail device of FIG. 1 in use.
Figure 9:
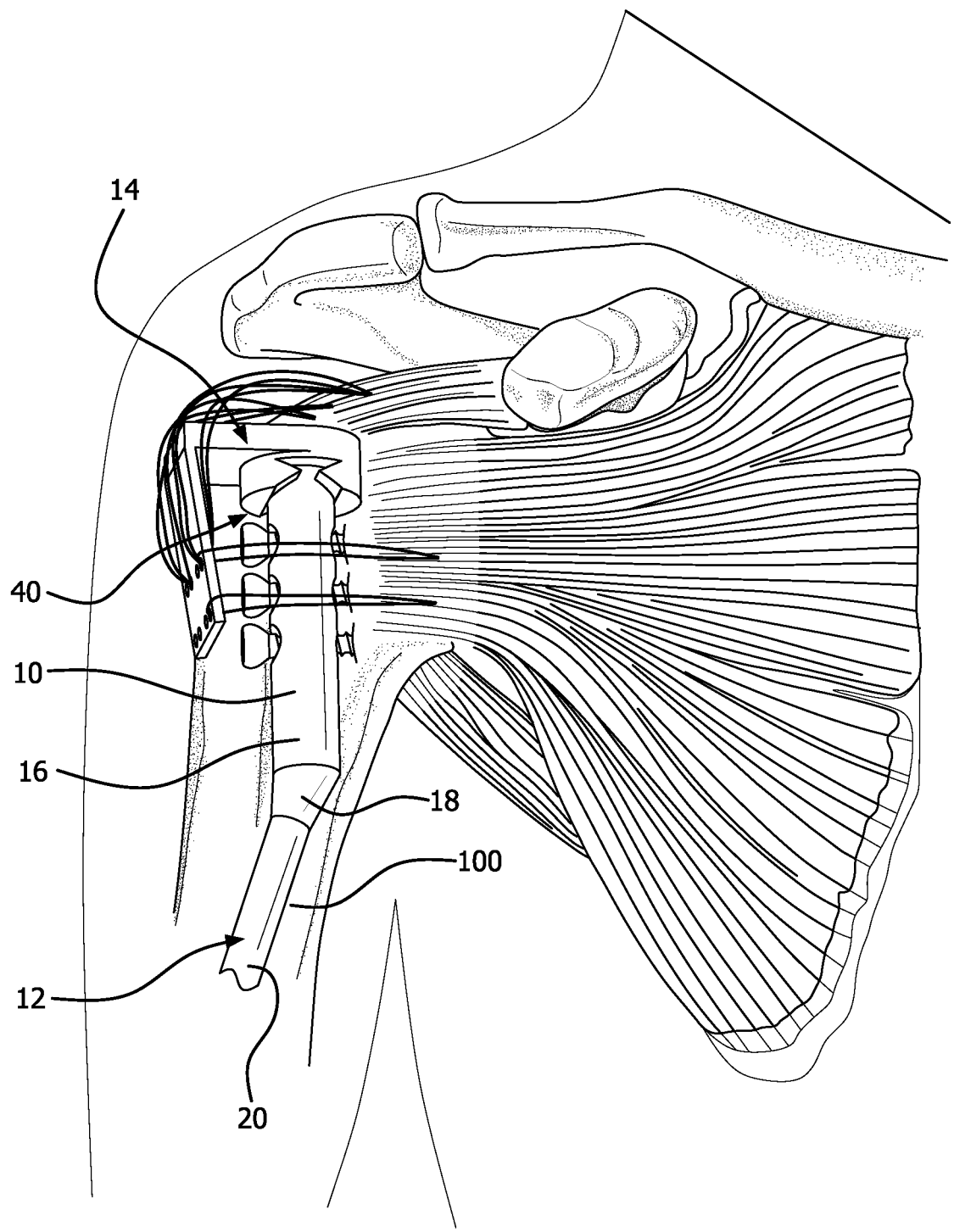
FIG. 9 is a side view of the humeral nail device of FIG. 1 in use.

Referring now to FIGS. 7-9, the humeral nail device 10 device includes a flexible intramedullary nail 12 for insertion into a humerus 100. The nail 12 takes form of an elongated unitary or integral cannulated body having a head 16, an angled frustocontical intermediate body portion 18, and a distal tip portion 20.

As shown in FIGS. 1-9, the nail 12 is inserted into the medullary canal of the humerus 100 to a position in which head 16 is in the proximal region 102 of the humerus 100, and the distal tip 20 is in the distal region 104 of the humerus 100. The head 16 is preferably cannulated or hollow along its length in order to provide an axial opening 22 which extends through the head 16. It is contemplated that the nail 12 be provided in three lengths of from approximately 240 mm to approximately 300 mm. The lengths will cover the sizes necessary to fix most humerus sizes. The nail 12 is inserted into the humerus 100 to a position in which the top end of the head 16 is adjacent to or, preferably, flush with, the entry opening formed in the humerus 100.

The humeral nail device 10 also provides a way to incorporate soft tissue injuries, such as rotator cuff tears into the repair with the use of the fixation bracket 14. The fixation bracket includes a top generally planar leg 32 and an inclined lateral leg 34 connected thereto. A plurality of suture holes 36 are provided in the lateral leg 34 as described in detail below. The diameter of the suture holes 35 are substantially smaller than screw openings and are sized to accommodate a typical suture. A connection 40 is provided in the lower surface 36 of the top leg 32 and the end 24 of the nail head 16. The connection preferable takes the form of a partial annulus 42 and a complementary shaped cylindrical tip 44 of the end of the head 16. Preferably, each complementary part 42 and 44 of the connection 40 is dovetailed as shown to secure the bracket 14 to the nail 12. In this way, the fixation bracket 14 can be easily fixed or secured to the top of the nail 12 prior to implantation and that enables soft tissue to be anchored securely to the healing bone.

An opening 50 is also provided through the top leg of the bracket coincident with the connection 40 and the axial opening 22 of the nail 12 which acts as a securing arrangement to secure the head 16 of the nail 12 to a device or a tool used for inserting the nail into the medullar canal. Several screw receiving openings 52 are located along the length of the nail head 16. The holes are 4 mm in diameter to accept cancellous bone screws. The holes are offset 5 degrees from each other. This is a common practice in screw and plate design. Screws that are placed in a straight line may propagate a fracture of worsen an existing fracture. Also offsetting the holes will allow for a wider purchase in the humeral head. The opening to receive screws 60 proximally is threaded and is about 3.5 to about 3.75 mm in diameter. And are adapted to receive the screws 60.

For fractures of the proximal region of the humerus, the medullary canal of the humerus is reamed with an appropriate tool or device according to conventional methods and procedures. The nail is inserted into the canal using conventional methods and appropriate tools and devices, including guiding devices, such as guiding wires. Following the insertion of the nail into the medullary canal, the screws are inserted through the bone and into the openings. For fractures of proximal humerus, the screws are inserted into the proximal openings.

The humeral nail device 10 combines the flexible nail 12 with proximal fixation screws 16. The humeral nail device 10 combines ease of insertion without the need for distally cross locking.

The flexibility of the nail 12 permits the nail 12 to become settled distally in the humerus 100. One preferred material to provide the requisite strength and flexibility is a titanium alloy, which would add to the flexibility of the nail. The proximal fixation implant 10 also provides a way to incorporate soft tissue injuries, such as rotator cuff tears into the repair with the use of the fixation tab 14. The fixation tab 14 can be easily fixed or secured to the top of the nail 12 prior to implantation and that enables soft tissue to be anchored securely to the healing bone.

The screws 16 are inserted through the nail 12 in the proximal portion with the aid of a targeting guide (not shown) and provide proximal fixation.

The nail 12 is an intramedullary device for humeral fractures. It is typically placed thru a small incision just above the top lateral corner of the humerus 100, using either an awl (not shown) or placed directly through an existing fracture fragment. An insertion tool (not shown) is used to place the nail 12 into the humerus 100 and helps guide the nail 12 into place.

The length of the nail 12 is chosen by the surgeon and is determined prior to surgery. The 12 nail is seated into the distal humerus either by hand or with the use of a mallet.

This nail system treats proximal humerus fractures (close to the shoulder joint), fractures in the shaft of the humerus, and proximal humeral fractures that also have soft tissue injuries such as a rotator cuff tear.

The nail 12 fixes a proximal humeral fracture with cross locking screws 60. The screws 60 are inserted with the use of an external guide. The screws 60 pass through the nail 12 and hold the fracture fragments together. The screws 60 are oriented at different angles, to improve the holding power in weak bone.

Typically, the nail 12 locks only proximally. Length and rotational control is maintained by driving the nail into distal metaphyseal bone (by the elbow). Also the nail 12 can be inserted into the intramedullary canal of the humerus without reaming the diaphysel bone. If there is no additional step of reaming the canal, surgical time is reduced.

FIGS. 10-16 show additional nail embodiments similar to the embodiment shown in FIGS. 1-9. Similar reference numerals refer to like reference numerals throughout.

The Clavicle Nail

Figure 10:
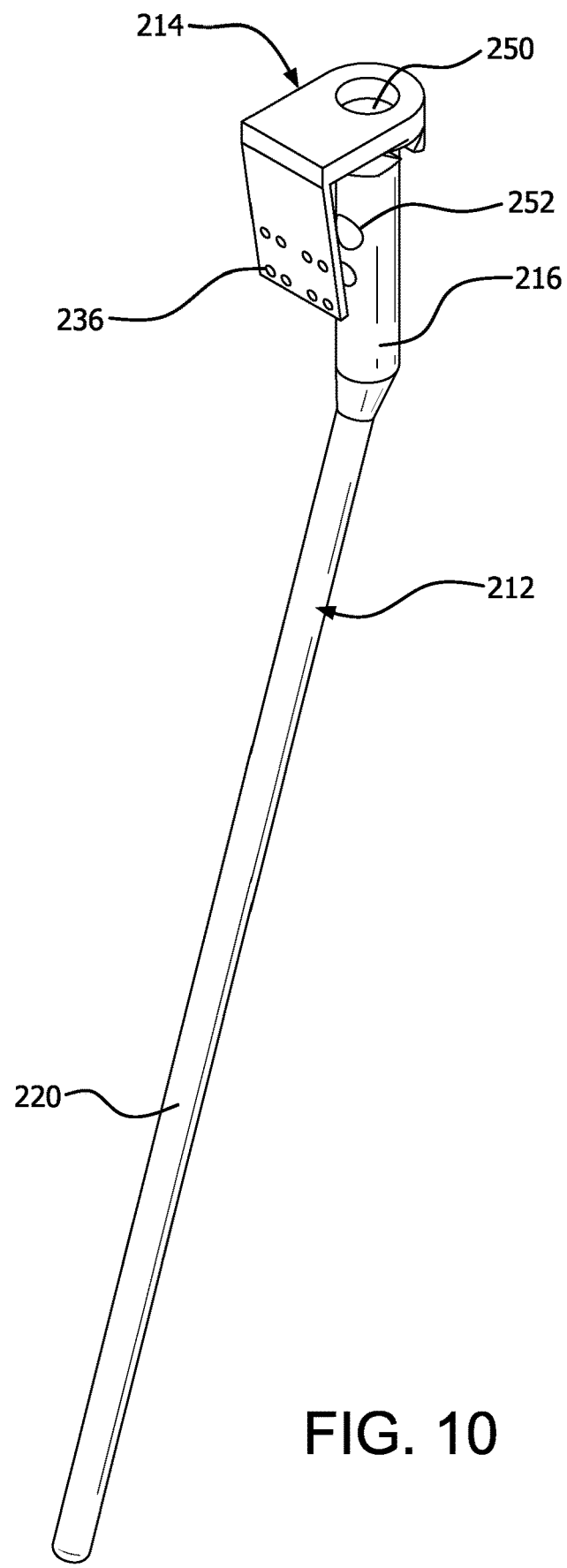
FIG. 10 is a front isometric view of a clavicle nail device in accordance with the present invention.
Figure 11:
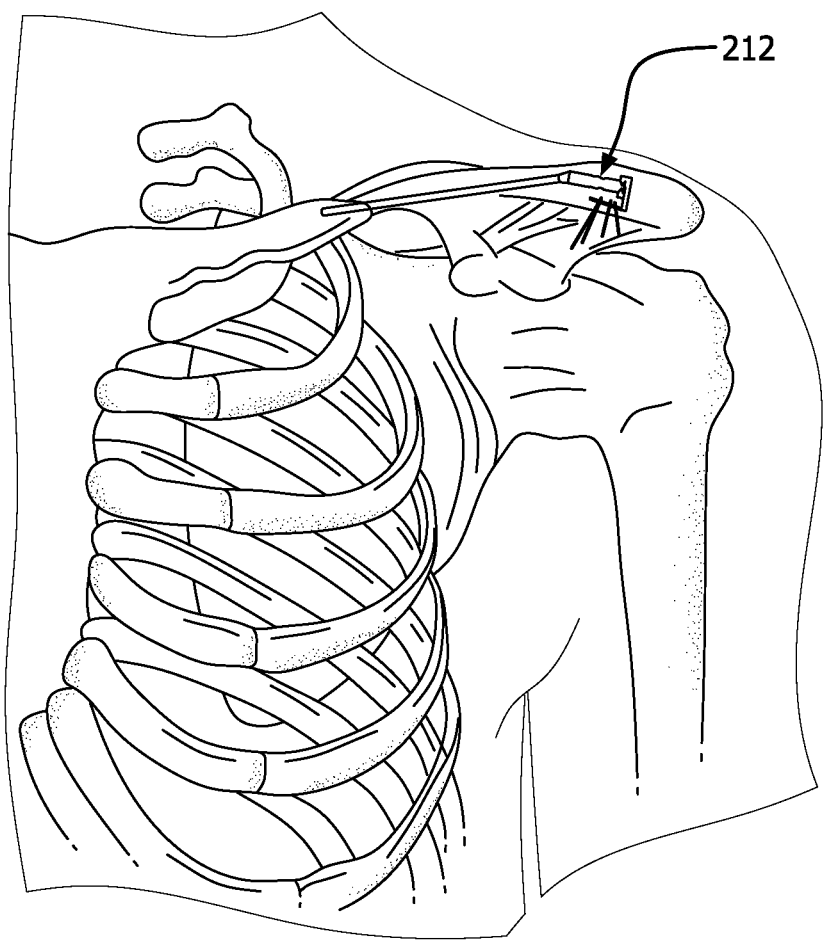
FIG. 11 is a front view of the clavicle nail device of FIG. 10 in use.

Referring now to FIGS. 10 and 11, the clavicle nail 212 is shown. The clavicle is similar to humeral nail 12.

In addition, the fixation tab aids in the suturing and healing of inferior structures, such as the coracoclavicular ligaments. The nail 212 also provides a way to incorporate soft tissue injuries into the repair with the use of the fixation bracket 214. A plurality of suture holes 236 are provided in the fixation bracket 214; the suture holes 236 are substantially smaller than the screw receiving openings described below. An opening 250 is also provided through the fixation bracket 214 coincident with the connection which acts as a securing arrangement to secure the head 216 of the nail 212 to a device or a tool (not shown) used for inserting the nail 212 into the clavicle. One or more threaded screw receiving openings 252 are located along the length of the nail head 216. The openings are about 4 mm in diameter to accept cancellous bone screws.

The clavicle nail 212 is inserted into the lateral end of the clavicle. Rigid fixation between the lateral nail end and the fixation tab 214 will be employed. The tab will extend laterally and then reach under the inferior clavicle surface. The suture holes 236 have holes to secure soft tissues in the region. The soft tissues are held in proper anatomic position while healing takes place.

Often, a clavicle has a lower piece attached to fractured bone and containing the strong coracoclavicular ligaments, which are made up of both the Trapezoid and Conoid ligaments. Even if the fracture is not around the ligaments (More medial and in the shaft), the fixation tab can hold the joint capsule between the acromion and the clavicle. Often these undersurface fractures need suturing as well.

The Radius Nail

Figure 12:
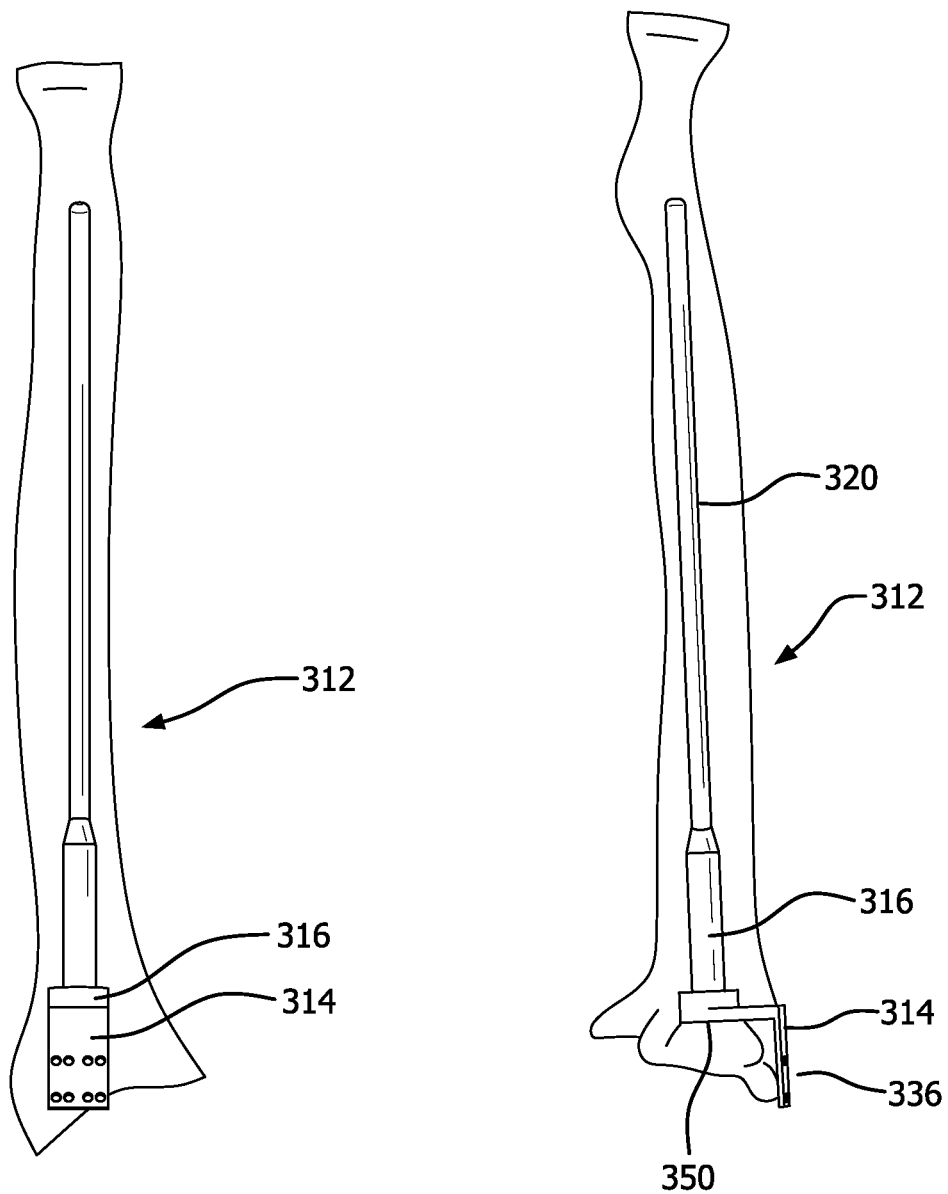
FIG. 12 is a front and side view of a radius nail device in use in accordance with the present invention.

Referring now to FIG. 12, the radius nail 312 is shown. The radius nail 312 is a flexible nail having either 3.5 or 3.0 mm in diameter. The nail 312 accepts two cross locking screws having a 1.8 mm diameter, so the distal portion has a larger diameter of about 5 mm. The fixation tab 314 extends axially up the dorsal radius and has small suture holes 336 for fixing ligaments.

As shown in FIG. 12, the radius nail 312 comprises head 316 and a distal tip 320. The radius nail 312 also provides a way to incorporate soft tissue injuries into the repair with the use of the fixation bracket 314. A plurality of suture holes 336 are provided in the fixation bracket 314; the suture holes are substantially smaller than the screw receiving openings described below. An opening 350 is also provided through the fixation bracket 314 which acts as a securing arrangement to secure the head 316 of the nail 312 to a device or a tool (not shown) used for inserting the nail 312 into the radius. One or more threaded screw receiving openings are located along the length of the nail head 316. The openings are about 4 mm in diameter to accept cancellous bone screws.

Depending on the fracture pattern the dorsal ligaments of the wrist joint between the dorsal (back of the hand side) distal radius and the scaphoid and lunate bones) are disrupted. Additionally, the soft tissue dorsal capsule is injured or torn by trauma to the wrist. These soft tissue supports are much weaker on the dorsum of the wrist then they are on the palm side. An intramedullary nail can be inserted on the dorsal side of the distal radius and a tab can be added to hold down the soft tissue. By use of the present invention, intramedullary radius fixation is achieved with a fixation tab that aids in the suturing and fixation of dorsal wrist ligaments while they heal.

The Fibula Nail

Figure 13:
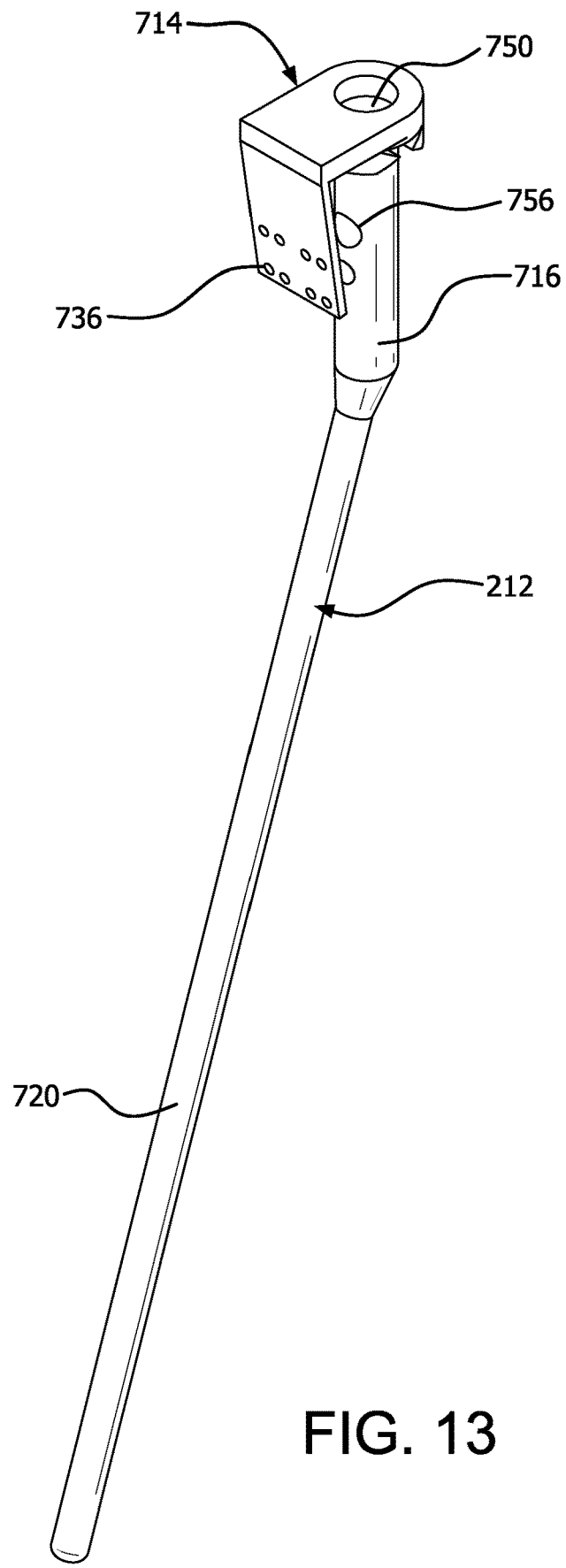
FIG. 13 is a front isometric view of a fibula nail device in accordance with the present invention.
Figure 14:
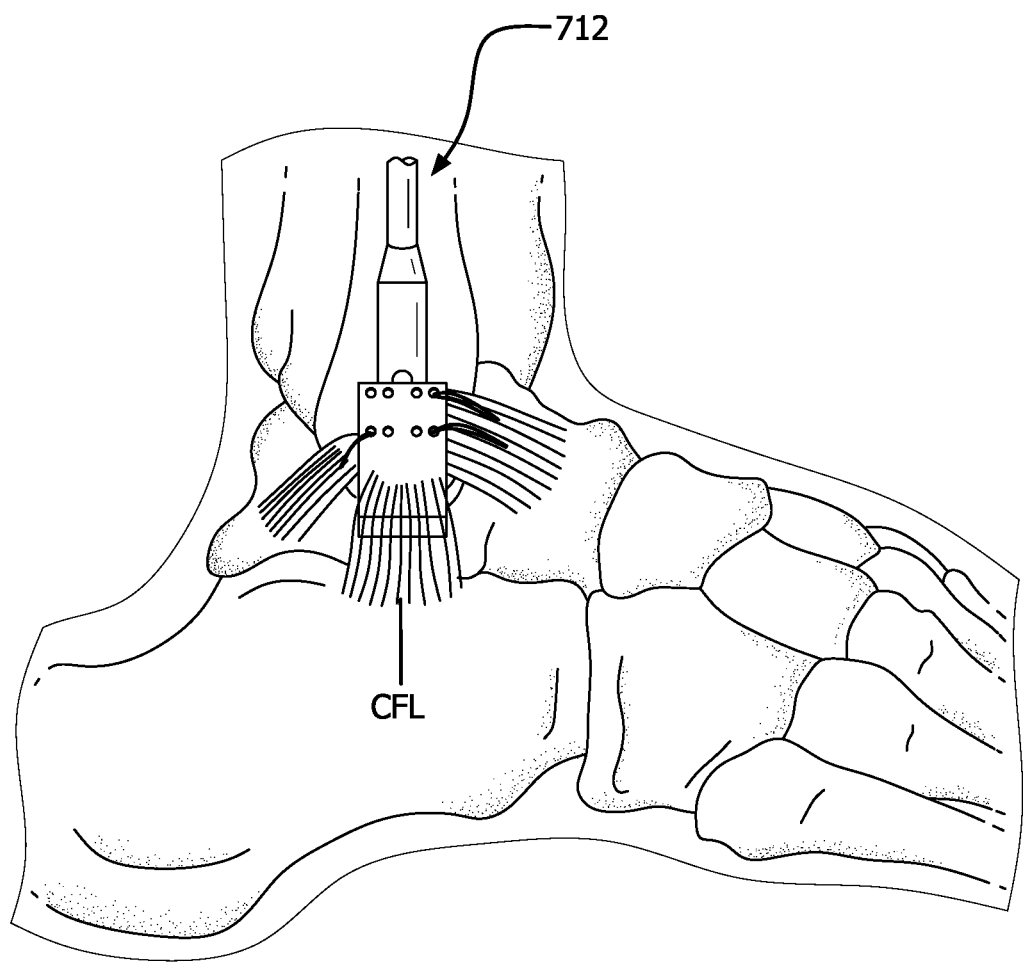
FIG. 14 is a side view of a fibula nail device of FIG. 13 in use.
Figure 15:
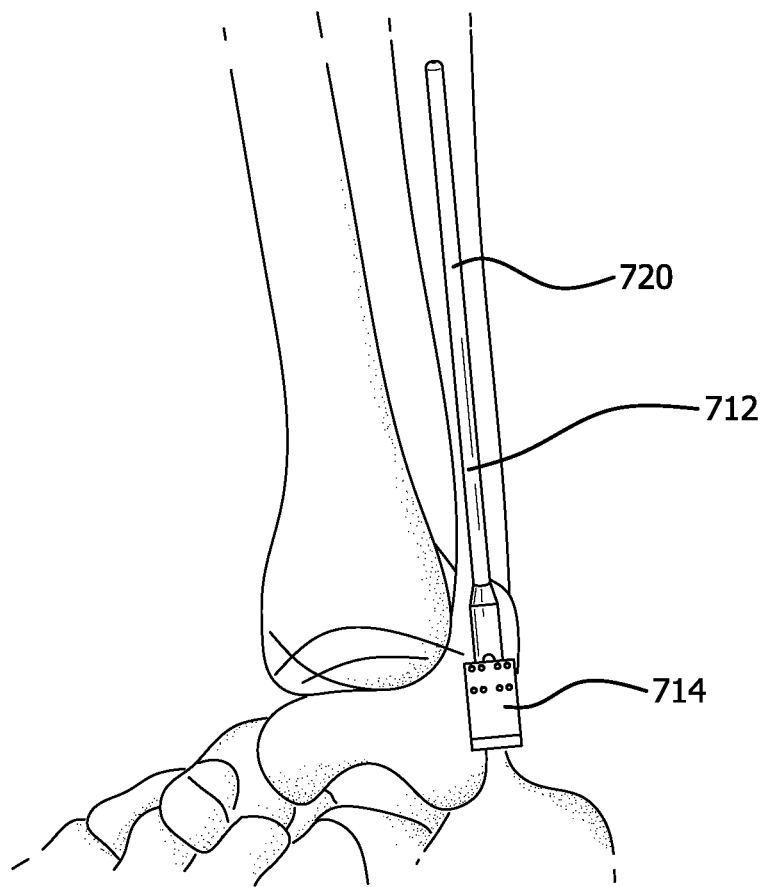
FIG. 15 is an opposite side view of a fibula nail device of FIG. 13 in use.

Referring now to FIGS. 13-15, the fibula nail 712 is shown. The fibula nail 712 accepts 5.0 mm cancellous screws. The fibula nail 712 includes suture holes to fix the ligaments.

As shown in FIGS. 13-15, the nail 712 comprises head 716 and a distal tip 720. The nail 712 also provides a way to incorporate soft tissue injuries into the repair with the use of the fixation bracket 714. A plurality of suture holes 736 are provided in the fixation bracket 714; the suture holes are substantially smaller than the screw receiving openings described below. A connection 740 is provided in the nail head 716 to secure the fixation bracket 714 to the nail 712 prior to implantation and enables soft tissue to be anchored securely to the healing bone. An opening 750 is also provided through the fixation bracket 714 coincident with the connection which acts as a securing arrangement to secure the head 716 of the nail 712 to a device or a tool (not shown) used for inserting the nail 712 into the bone. One or more threaded screw receiving openings 752 are located along the length of the nail head 716. The openings are about 4 mm in diameter to accept cancellous bone screws 760.

Fibula implant will consist of a nail that employs holes for cross locking screws for syndesmosis screws or a tight rope. The outside of the bone will have a tab (much like the humeral implant already patented) but upside down. The tab will allow for sutures to be used to hold the complex ligaments of the distal lateral ankle.

There are many techniques for fixing both the lateral ligaments around the ankle and also for repairing the syndesmosis ligaments. These techniques are evolving and it is a new topic for fracture fixation. Since fibula nails are hard to use they are not very popular, this may be in part why there is no tab specifically for the fibula. Also there is a soft tissue room problem.

A nail can be used for bone fixation and a tab can be used to hold and repair lateral and syndesmosis ligaments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A surgical nail device for a clavicle, comprising
    a flexible nail adapted to be inserted into a medullary canal of a clavicle, the flexible nail having an elongated distal tip body and a proximal head, the flexible nail being configured and sized to be inserted into a lateral end of the clavicle, a longitudinal axis of the elongated body being at an acute angle relative to a longitudinal axis of the head, the elongated body being sized such that a top of the head is substantially flush with an entry opening in the clavicle when the flexible nail is inserted into the medullary canal during use, wherein a plurality of screw receiving openings are located along the length of the head, the screw receiving openings having a diameter of 4 mm; and
    a fixation bracket attached via a connector to the head, the bracket having a plurality of holes having a diameter substantially smaller than the screw receiving openings and sized to accept sutures therein to enable soft tissue and coracoclavicular ligaments to be anchored securely to the clavicle during use, the fixation bracket having a top plate and a lateral plate extending therefrom at an acute angle back towards the elongated body of the flexible nail to extend laterally to reach under an inferior surface of the clavicle, the connector having a first part extending outwardly from the top of the head and coaxially along the longitudinal axis of the head portion, and a complementary second part formed in the top plate.

2. The surgical nail device in accordance with claim 1 wherein one of the first and second parts being a partial annulus and the other of the first and second parts being a complementary extending tip.

3. The surgical nail device in accordance with claim 2 wherein the connector being a circular dovetailed connection.

4. The surgical nail device in accordance with claim 2 wherein the flexible nail has a frustoconical intermediate portion connecting the distal tip body and the head, a longitudinal axis of the intermediate portion being coincident with the longitudinal axis of the distal tip body.

5. The surgical nail device in accordance with claim 4 wherein the screw receiving openings being offset by 5 degrees from each other.

6. The surgical nail device in accordance with claim 1 wherein the top plate has a tool opening coincident with a connector opening in the flexible nail to receive an insertion tool therein.

7. The surgical nail device in accordance with claim 6 wherein the flexible nail having a length between 240 mm and 300 mm and the flexible nail is made from a titanium alloy material.

8. A surgical nail device for a fibula, comprising
    a flexible nail adapted to be inserted into a medullary canal of a fibula, the flexible nail having an elongated distal tip body and a proximal head, the flexible nail being configured and sized to be inserted into a lateral end of the fibula, a longitudinal axis of the elongated body being at an acute angle relative to a longitudinal axis of the head, the elongated body being sized such that a top of the head is substantially flush with an entry opening in the fibula when the flexible nail is inserted into the medullary canal during use, wherein a plurality of screw receiving openings are located along the length of the head, the screw receiving openings having a diameter of 4 mm; and
    a fixation bracket attached via a connector to the head, the bracket having a plurality of holes having a diameter substantially smaller than the screw receiving openings and sized to accept sutures therein to enable soft tissue and ligaments of a distal lateral ankle to be anchored securely to the fibula during use, the fixation bracket having a top plate and a lateral plate extending therefrom at an acute angle back towards the elongated body of the flexible nail to extend laterally to reach under an inferior surface of the fibula, the connector having a first part extending outwardly from the top of the head and coaxially along the longitudinal axis of the head portion, and a complementary second part formed in the top plate.

9. The surgical nail device in accordance with claim 8 wherein one of the first and second parts being a partial annulus and the other of the first and second parts being a complementary extending tip.

10. The surgical nail device in accordance with claim 9 wherein the connector being a circular dovetailed connection.

11. The surgical nail device in accordance with claim 9 wherein the flexible nail has a frustoconical intermediate portion connecting the distal tip body and the head, a longitudinal axis of the intermediate portion being coincident with the longitudinal axis of the distal tip body.

12. The surgical nail device in accordance with claim 8 wherein the top plate has a tool opening coincident with a connector opening in the flexible nail to receive an insertion tool therein.

13. A surgical nail device for a radius, comprising
a flexible nail adapted to be inserted into a medullary canal of a radius, the flexible nail having an elongated distal tip body and a proximal head, the flexible nail being configured and sized to be inserted into a lateral end of the radius, a longitudinal axis of the elongated body being at an acute angle relative to a longitudinal axis of the head, the elongated body being sized such that a top of the head is substantially flush with an entry opening in the radius when the flexible nail is inserted into the medullary canal during use, wherein a plurality of screw receiving openings are located along the length of the head, the screw receiving openings having a diameter of 4 mm; and
a fixation bracket attached via a connector to the head, the bracket having a plurality of holes having a diameter substantially smaller than the screw receiving openings and sized to accept sutures therein to enable soft tissue and dorsal ligaments of a wrist to be anchored securely to the radius during use, the fixation bracket having a top plate and a lateral plate extending therefrom axially up a dorsal portion of the radius, the connector having a first part extending outwardly from the top of the head and coaxially along the longitudinal axis of the head portion, and a complementary second part formed in the top plate.

* * * * *